United States Patent
Fields

(10) Patent No.: US 11,167,023 B2
(45) Date of Patent: Nov. 9, 2021

(54) METHOD OF TREATING MAMMALS DISPLAYING SEVERE NEUROLOGICAL SYMPTOMS OF ADVANCED CANINE DISTEMPER VIRUS INFECTION USING NDV-INDUCED SERUM

(71) Applicant: DANCLAY Properties, LLC, Florence, AL (US)

(72) Inventor: Anupama Y. Fields, Florence, AL (US)

(73) Assignee: Danclay Properties, LLC, Florence, AL (US)

( * ) Notice: Subject to any disclaimer, the term of this patent is extended or adjusted under 35 U.S.C. 154(b) by 0 days.

(21) Appl. No.: 16/236,258

(22) Filed: Dec. 28, 2018

(65) Prior Publication Data

US 2020/0206338 A1   Jul. 2, 2020

(51) Int. Cl.
| | |
|---|---|
| A61K 39/12 | (2006.01) |
| A61K 35/16 | (2015.01) |
| C07K 14/13 | (2006.01) |
| A61P 25/08 | (2006.01) |
| A61P 31/14 | (2006.01) |
| C07K 16/06 | (2006.01) |
| A61K 39/00 | (2006.01) |

(52) U.S. Cl.
CPC .............. *A61K 39/12* (2013.01); *A61K 35/16* (2013.01); *A61P 25/08* (2018.01); *A61P 31/14* (2018.01); *C07K 14/13* (2013.01); *C07K 16/06* (2013.01); *A61K 2039/54* (2013.01); *A61K 2039/552* (2013.01)

(58) Field of Classification Search
None
See application file for complete search history.

(56) References Cited

U.S. PATENT DOCUMENTS

| | | | |
|---|---|---|---|
| 2,202,435 A | 5/1940 | Shoetensack | |
| 3,285,817 A | 11/1966 | Slater | |
| 3,836,648 A | 9/1974 | Chang | |
| 5,000,951 A | 3/1991 | Bass et al. | |
| 4,992,272 A | 12/1991 | Bass et al. | |
| 5,807,840 A | 9/1998 | Hirschman | |
| 6,383,741 B2 | 5/2002 | McMichael | |
| 6,719,984 B1 | 4/2004 | Ansley | |
| 8,052,971 B2 | 11/2011 | Meyer | |
| 2017/0121408 A1* | 5/2017 | LaVallee | C07K 16/2803 |
| 2020/0206338 A1* | 7/2020 | Fields | C07K 14/13 |

OTHER PUBLICATIONS

Breed Weight Chart from: www.akc.org/expert-advice/nutrition/breed-weight-chart/ by AKC Staff, published online May 11, 2017.*
"Canine Distemper (CDV)" by Shelter Medicine from the School of Veterinary Medicine at the University of Wisconsin-Madison; Jul. 10, 2010).*
Perrone et al. (The Canadian Journal of Veterinary Research. 2010; 74: 214-217.*
Loutit et al. (British Medical Journal. 1945; 759-760).*
Bond E. Newcastle Disease Vaccine (NDV) treatment for canine distemper. Jan. 15, 2010. Available at www.edbond.com/NDV_packet.pdf (last accessed Jul. 25, 2018).
Bond E. Report on the Effectiveness of NDV Treatments. Feb. 13, 2016. Available at www.kindheartsinaction.com/archives/1353 (last accessed Jul. 25, 2018).
Bond E. Using the NDV Before Seizures. Jan. 11, 2010. Available at www.kindheartsinaction.com/archives/313 (last accessed Jul. 25, 2018).
Harkin K, Wilkerson M. Evaluation of the therapeutic efficacy and changes in cytokines in cerebrospinal fluid and plasma in dogs with canine distemper encephalitis treated with intrathecal live Newcastle Disease Virus vaccine [Research Proposal]. 2014. Available at www.maddiesfund.org (last accessed Jul. 25, 2018).
Sears A. NDV-induced Serum. 2011. Available at www.kindheartsinaction.com/archives/82 (last accessed Jul. 25, 2018).
Vahlenkamp T. Canine Distemper and Other Canine Viral Infections, in Textbook of Veterinary Internal Medicine. 2016. pp. 1006-1009.
Kind Hearts in Action, "Distemper dogs treated with NDV", https://www.kindheartsinaction.com/archives/1641, Apr. 26, 2011 (4 pages).
Kind Hearts in Action, "Welcome to Kind Hearts in Action", https://www.kindheartsinaction.com/, undated (2 pages).
Kind Hearts in Action, "Distemper dogs saved with serum or NDV", https://www.kindheartsinaction.com/archives/143, Nov. 8, 2009 (8 pages).

* cited by examiner

*Primary Examiner* — Shanon A. Foley
(74) *Attorney, Agent, or Firm* — Finnegan, Henderson, Farabow, Garrett & Dunner, LLP

(57) ABSTRACT

This application discloses methods, compositions, and articles of manufacture for using NDV-induced serum to treat non-human mammals, including dogs, displaying severe neurological symptoms of advanced canine distemper virus (CDV) infection. An off-the-shelf chicken vaccine is injected into two or more healthy mammals, of the same species as the sick animal, to provoke an immune response. After allowing several hours for the immune response to develop, blood is drawn from the healthy mammals and centrifuged to obtain serum. This "NDV-induced serum" can be injected into a mammal of the same species displaying severe neurological symptoms of advanced CDV infection on a prescribed schedule to bolster the sick animal's immune responses, preferably leading to clearance of the virus without the need for a spinal tap, which is the standard treatment for advanced CDV infection in mammals.

22 Claims, No Drawings

METHOD OF TREATING MAMMALS DISPLAYING SEVERE NEUROLOGICAL SYMPTOMS OF ADVANCED CANINE DISTEMPER VIRUS INFECTION USING NDV-INDUCED SERUM

Canine distemper virus (CDV) causes a measles-like illness in dogs, weasels, raccoons, bobcats, larger cats, and other mammals. CDV spreads quickly by coughing and sneezing, in addition to transmission through urine, vomit, and/or feces. The domestic dog serves as the focus of discussion of the invention, but the invention is not limited to the species listed.

Although a vaccine for CDV came into use more than 50 years ago, CDV runs rampant in many countries. In the United States, dog owners widely adhere to vaccination guidelines and CDV outbreaks tend to occur where unvaccinated dogs are in close quarters, such as in animal shelters. CDV typically takes 1-3 weeks to incubate, with virus shedding in all bodily excretions beginning 7-10 days following infection. An infected dog may be contagious for up to 3 months. Because treatment for viral illness requires isolation, supportive care (e.g., parenteral administration of fluids for dehydrated animals), and stringent biosecurity measures, many shelters in the United States opt to euthanize all dogs onsite when confronted with a suspected case of CDV.

CDV causes systemic infection in epithelial tissues throughout the body. Early on, viral replication takes place in the cells lining the mouth and nose, leading to the hallmark symptoms of cough and eye/nose discharge, before spreading to the bloodstream, liver, digestive tract, and eventually the central nervous system (CNS). Fever accompanies increased virus production, as can anorexia, dehydration, and lethargy. Over 80% of puppies and 50% of adult dogs infected with CDV die. Yet despite the substantial damage it inflicts, the single-stranded RNA virus responsible for CDV cannot survive long outside a live host, given its susceptibility to UV light, drying, heat, and routine disinfectants.

When the virus finds a host, the outcome of CDV infection typically depends on a range of factors, including the host's age, robustness of its immune system, and virulence of the particular CDV strain. Animals with weak immune systems often develop more extensive viral infections (and secondary bacterial infections like pneumonia), which often lead to death. Animals that recover from the initial respiratory symptoms typically harbor the virus and will most likely develop severe CNS symptoms associated with the advanced stage of distemper. And even with animals having immune responses robust enough to stave off initial symptoms of infection, CNS symptoms may eventually develop. Neurologic symptoms can manifest 1-3 weeks after recovery from upper respiratory symptoms. Telltale signs that the distemper virus has established itself in the CNS include limb paralysis (paraparesis), seizures, jerky muscles (myoclonus), and loss of full control of movement (ataxia), among other symptoms.

In addition to observing clinical manifestations of CDV infection, additional means of diagnosis include, but are not limited to, canine distemper polymerase chain reaction (PCR) (whole blood, spinal fluid, or conjunctival scrape), spinal fluid analysis, canine distemper antibody assays (spinal fluid, serum), spinal fluid analysis, NDV PCR (spinal fluid), and the like (Harkin & Wilkinson). PCR tests such as IDEXX RealPCR™ can distinguish CDV infection from CDV vaccination in dogs.

In the wild, CDV causes illness in a variety of mammalian species, including canids (domestic dog, wolf, coyote, fox, jackal, dingo, and the like), mustelids (weasels, badgers, otters, minks, martens, polecats, wolverines, and the like), procyonids (raccoons, coatis, olingos, olinguitos, ringtails, cacomistles, kinkajous, and the like), and large felids (bobcats, wildcats, ocelots, lynxes, cheetahs, servals, leopards, snow leopards, cougars, pumas, tigers, lions, and the like), and other species. As noted above, this description will primarily refer to domestic dogs, but the reader should not infer any limitation as to the species listed. The other most widely domesticated mammal, the domestic cat, does not fall ill due to CDV, but instead can fall prey to feline distemper virus.

TECHNICAL FIELD

The embodiments of the invention described and claimed here fall under the field of veterinary biologics and treatment of viral disease in mammals.

BACKGROUND ART

The first description of canine distemper as an infectious disease in dogs was published in 1905 and its viral origin was clearly demonstrated by 1926. By 1940, there was a patented process for preparation of canine distemper vaccine (U.S. Pat. No. 2,202,435 A), and by 1965, a patented method of using a measles vaccine to induce distemper resistance in dogs (U.S. Pat. No. 3,285,817 A).

By at least 1998, it was disclosed that CDV could be treated by administration of antibodies parenterally using, e.g., Product R, a peptide-nucleic acid preparation (U.S. Pat. No. 5,807,840 A). U.S. Pat. No. 6,383,741 B2 disclosed treatment capable of relieving CDV symptoms by administering attenuated canine distemper or measles virus. See also U.S. Pat. Nos. 4,992,272 A and 5,000,951 A for vaccines using attenuated CDV. Similarly, U.S. Pat. No. 3,836,648 A teaches a therapeutic CDV agent having a specific type of inactivated bacterium.

As for eliciting immune response in one animal to treat another, U.S. Pat. No. 8,052,971 B2 teaches immunizing a healthy mammal with an enteric disease antigen and subsequently harvesting antibodies to that antigen from the plasma of the healthy mammal and, in turn, orally administering the antibody-rich plasma to another mammal suffering from the enteric disease. In a similar vein, U.S. Pat. No. 6,719,984 B1 describes immunostimulation of a mammal with immune system components in a specific molecular weight range, which were obtained from the blood of another mammal.

With regard to Newcastle Disease Vaccine (NDV), it has been known since the 1970s that animals with early respiratory stage CDV infection respond well to injection of serum harvested from a healthy animal of the same species earlier injected with the NDV chicken vaccine. See, e.g., "NDV Serum Treatment for Dogs." Protocols for preparing so-called "NDV-Induced Serum" appear to have been readily available on the internet since at least 2009, e.g., "NDV-Induced Serum" available at www.kindheartsinaction.com/archives/82.

Published compilations of anecdotal reports of veterinarians' use of NDV-induced serum for treating early (that is, respiratory) CDV infection, include one case where the serum was injected into the spinal fluid to treat symptoms of advanced CDV infection, i.e., CDV infection with severe neurological symptoms. Notably, however, this same report states that the so-called "NDV spinal tap" saves less than half of dogs with advanced CDV infection (see "Report on Effectiveness," page 4, last paragraph). Similarly, "Using the NDV Before Seizures" describes injecting NDV into dogs sick with CDV to prevent seizures—rather than into healthy dogs for serum harvest first—but only where dog is older than 12 weeks and has not started having seizures.

Technical Problem

Spinal tap administration of NDV vaccine has been the standard treatment for dogs displaying severe neurological symptoms of advanced CDV infection, such as frequent seizures. Spinal tap procedures, however, require advanced veterinary skill and operating facilities, and carry concomitantly greater costs, as well as the risk of infecting the spinal fluid of the subject and causing serious complications such as meningitis (Harkin & Wilkerson). Preparation and administration of NDV-induced serum is widely known but has only been used for treating early respiratory symptoms of CDV. Until now, there has not been an effective, low-cost method for treating advanced stages of CDV infection in dogs displaying late neurological symptoms.

Accordingly, there exists a need in the art for compositions, articles of manufacture, and methods for treating mammals, especially domestic dogs, exhibiting advanced stages of CDV infection. In addition, there exists a need in the art for compositions, articles of manufacture, and methods for treating these mammals without resorting to spinal tap procedures.

SUMMARY OF INVENTION

This invention aids in resolving these needs in the art.

In one embodiment, this invention provides a method of treating a mammal having neurological symptoms of canine distemper virus (CDV) infection. The mammal is treated by administering two or more separate compositions that are not mixed, each comprising serum collected from a healthy member of the same species earlier injected with Newcastle Disease Vaccine (NDV). The treated mammal survives and would test negative for CDV infection using widely available lab testing such as PCR. Examples of mammals that can be treated according to the invention include a canid, a mustelid, a procyonid, or a felid that is larger than a domestic cat.

Examples of species of mammals that can be treated include a domestic dog, wolf, coyote, fox, jackal, dingo, other dog-like mammal, a weasel, badger, otter, mink, marten, polecat, wolverine, other weasel-like mammal, a raccoon, coati, olingo, olinguito, ringtail, cacomistle, kinkajou, other raccoon-like mammal, a bobcat, wildcat, ocelot, lynx, cheetah, serval, leopard, snow leopard, cougar, puma, tiger, lion, or other cat-like mammal that is larger than a domestic cat.

In another embodiment, this invention provides a method of treating a dog with neurological symptoms of canine distemper virus (CDV) infection, which comprises administering to the dog two or more separate compositions that are not mixed, each comprising serum collected from a healthy dog earlier injected with Newcastle Disease Vaccine (NDV). Preferably, the dog is a domestic dog and treatment is carried out without spinal tap procedures. Examples of healthy dogs earlier injected with NDV that can be employed in the invention are dogs, 10-48 months old, of mixed breed, such as a black Labrador mix or border collie mix, weighing 40-120 pounds, without any autoimmune disorders, mange, mites, arthritis, or the like, and optionally unaltered, i.e., neither spayed nor neutered.

This invention also provides an article of manufacture for treating a mammal with neurological symptoms of CDV infection. The article of manufacture comprises two or more separate compositions that are not mixed, each comprising serum collected from a healthy member of the same species earlier injected with Newcastle Disease Vaccine (NDV), wherein treating the mammal with the compositions results in the mammal surviving and becoming not infectious for canine distemper.

This invention provides straightforward, user-friendly ways to treat mammals, especially domestic dogs, showing severe neurological symptoms of advanced CDV infection. The compositions, articles of manufacture, and methods of the invention require less equipment than traditional spinal tap treatment and consequently avoid higher costs and risks of infecting spinal fluid.

DETAILED DESCRIPTION

This invention provides compositions, articles of manufacture, and methods for treating a mammal, preferably a domestic dog, that exhibits neurological symptoms of canine distemper virus infection. As used herein, the term canine distemper is used in its conventional sense as referring to a contagious and serious disease caused by a single-stranded virus designated canine morbillivirus.

CDV infections cause progressively more severe neurological symptoms over time:
Initial Stage—typified by "upper respiratory symptoms," such as persistent cough, high fever, red eyes, watery or green-colored discharge from eyes and nose, lethargy, and often vomiting, diarrhea, and loss of interest in food;
Intermediate Stage—typified by fairly mild "early neurological symptoms," such as occasional seizures, mild paralysis, mild myoclonus; and
Advanced Stage—typified by more severe "late neurological symptoms," such as frequent seizures, fits, paralysis, and even hysteria attacks.

The mammal treated for CDV infection and the healthy members of the same species earlier injected with the NDV can be selected from a canid, a mustelid, a procyonid, or a felid that is larger than a domestic cat. The canid can be a domestic dog, wolf, coyote, fox, jackal, dingo, or other dog-like mammal. The mustelid can be a weasel, badger, otter, mink, marten, polecat, wolverine, or other weasel-like mammal. The procyonid can be a raccoon, coati, olingo, olinguito, ringtail, cacomistle, kinkajou, or other raccoon-like mammal. When the mammal is a felid, the felid can be a bobcat, wildcat, ocelot, lynx, cheetah, serval, leopard, snow leopard, cougar, puma, tiger, lion, or other cat-like mammal that is larger than a domestic cat.

Preferably, the mammal is a domestic dog and the healthy members of the same species earlier injected with the NDV are domestic dogs. As used herein, a domestic dog is a member of the genus *Canis* that has been domesticated by man, also known as *Canis* (lupus) *familiaris* or, simply, a dog.

When the mammal being treated and the donor mammals are domestic dogs, healthy member of the same species would be healthy donor dogs. Such dogs can be 10-48 months old, mixed breed, 40-120 lbs, preferably unaltered, and healthy, without any autoimmune disorders, mange, mites, arthritis, or the like. In particular, two or more donor dogs should be used for each batch of serum, i.e., NDV-induced serum from two or more healthy dogs will be used to treat one sick dog. The donor dogs are preferably free of immune suppressants, such as corticosteroids and/or antihistamines, for at least 14 days before this procedure. For NDV-induced serum to have potent effects, any mixed breed may be used, but black lab mixes and border collie mixes are preferable; pure breeds or individuals known to have immune deficiency problems are less preferable.

The reader should not infer that the embodiments of the invention disclosed here are limited to domestic dogs; for this discussion about a healthy member of the same species, dogs are merely an example.

An effective amount of NDV-induced serum, or therapeutically effective derivative(s) made from it, can be administered to an animal by mouth in tablet or capsule form, by injection—intravenously (IV), parenterally, or subcutaneously—in liquid form, or by any pharmaceutically acceptable formulation having helpful characteristics such as enhanced taste, stability, convenience, solubility, and so on. These various administration forms may be produced by any methods well known in the pharmaceutical arts.

To facilitate treating a sick animal by mouth with NDV-induced serum, or therapeutically effective derivative(s) made from it, an inert diluent combined with an edible carrier can be employed, as well as encapsulation in gelatin or compression into tablets. Combination with excipients can allow for tablets, capsules, suspensions, wafers, elixirs, semi-solids, granules, soft chews, chewable tablets, and so forth to produce stable dosage forms. These preparations should have at least 0.1% NDV-induced serum, or therapeutically effective derivative(s) made from it, but this amount can range widely form to form, so long as a suitable dosage results. Forms that animals will readily consume on their own are favored.

Capsules, pills, tablets, etc., can contain: a binder like gelatin, microcrystalline cellulose, or natural gum; an excipient like lactose or starch; a lubricant like magnesium stearate; a disintegrating agent like corn starch or alginic acid; a glidant like colloidal silicon dioxide; or a flavoring agent like those found in animal feed, such as powders having meat, chicken, or sweet molasses flavors. Capsular forms may further contain a carrier liquid like a fatty oil. The dosage units form can also be modified by coating, e.g., enteric coating, as well as the addition of dyes, colorings, and preservatives. In all instances, the resulting compositions should be non-toxic, pharmaceutically pure enough for use in animals, and suitable for delivery of a therapeutically effective dosage.

For purposes of therapeutic administration by injection—whether IV, parenterally, or subcutaneously—the NDV-induced serum, or therapeutically effective derivative(s) made from it, can be suspended or dissolved in a suitable medium or injected as 100% serum obtained from centrifuging blood from a donor animal. Forms requiring refrigeration should be cooled appropriately and may be frozen, so long as the dosage unit retains therapeutic effectiveness. Solutions or suspensions should have at least 0.1% NDV-induced serum, or therapeutically effective derivative(s) made from it, but the percentage may range widely, so long as a suitable dosage results.

With the present invention, the most preferable form for therapeutic administration of NDV-induced serum, or therapeutically effective derivative(s) made from it, is a composition comprising serum obtained by centrifuging blood from a healthy donor as detailed below for treating a mammal having neurological symptoms of CDV. The composition comprises serum collected from a healthy member of the same species earlier injected with Newcastle Disease Vaccine (NDV), also referred to here as donor mammals, donor animals, donor dogs, or simply donors.

NDV is an infectious viral disease known to infect commercial and village chickens that can be controlled by the use of vaccines. There are different types of NDV vaccines, such as live vaccines and killed vaccines. In addition, there are different vaccine strains, such as lentogenic strains that are non-virulent and virulent strains that are mesogenic (intermediate virulence) or velogenic (highly virulent). And there are commercial versions of most of these strains. Specifically exemplified here is the La Sota strain, B1 Type. But other vaccines type may be considered.

Injecting NDV into a healthy donor dog will provoke an immune response, and NDV-induced serum is harvested from each donor dog's blood. Serum from each donor animal is kept separate from serum of each of the other donor animals for separate, sequential injections into an animal sickened by CDV infection, i.e., serum from different donor animals is not combined. Further, after serving as a donor animal, the same animal should never be used again for collection of NDV-induced serum, i.e. reinjected with NDV as detailed below.

Preparing and Collecting NDV-Induced Serum from Healthy Dogs

Preparation of NDV-induced serum generally follows publicly available guidelines, such as those mentioned above. However, specific differences exist and are detailed below.

Preferably, two or more donor dogs should be used for collecting each batch of serum, i.e., NDV-induced serum from two or more healthy dogs will be used to treat one sick dog without mixing or combining the serum or any composition comprising the serum, i.e., serum from different donor dogs should never be mixed. Preferably, the donor dogs should be free of immune suppressants, such as corticosteroids and/or antihistamines, for at least 14 days before this procedure.

Aliquots of Newcastle Disease Vaccine, for example, live, La Sota strain, may be purchased commercially in lyophilized form (e.g., B1 Type, La Sota Strain, Live Virus; Pfizer® List No. 1510855PFE: 10×5,000 Doses). Add an appropriate diluent, such as Ringer's sodium lactate solution ("RL") or the like, to the NDV in the amount of 5-7 milliliters ("mis") or most preferably about 6 mls. Immediately refrigerate the resulting solution. Anesthetize the donor dog and insert a catheter in its jugular vein; inject 5-7 mls or most preferably about 6 mls of NDV solution via catheter (or equivalent amount of virus if diluted differently), and immediately flush IV with at least 5-7 mls or most preferably about 6 mls RL.

Because at least 2 donor animals are required, it is recommended that the timing of injections be staggered to allow sufficient time for anesthesia and pulling blood from multiple donor animals.

For harvest of NDV-induced serum in dogs, for example, anesthetize one donor dog 9-13 hours post-NDV injection, or more preferably 10-12 hours post-NDV injection, or most preferably just prior to the $11^{th}$ hour post-NDV injection. Place the jugular catheter and start IV fluid. Draw blood under sterile conditions most preferably approximately 11 hours post-NDV injection and inject into vials without any clotting agent(s). Allow blood to clot, and then centrifuge at a speed sufficient to isolate NDV-induced serum without rupturing red blood cells. This serum can be used without further processing, i.e., it may be considered a composition comprising serum suitable for injection without addition of any further components. In the same vein, the serum may be further processed by any methods well known in the pharmaceutical arts to produce any form for administration that remains therapeutically effective, e.g., suspended or dissolved in a suitable medium as discussed above.

The amount of blood drawn should fall within generally accepted guidelines (i.e., 1-2% of body weight, with IV fluid replacement for draws higher than 1%). For example, a 1% draw from a 100-lb (45-kg) dog would be 450 mls, with fluid replacement for a larger draw—not to exceed 900 mls. Isolated NDV-induced serum may be stored in sterile containers under refrigeration for up to 3 months, or longer if frozen.

Preparations for Treating CDV Infection Using NDV-Induced Serum

Initial Stage (Upper Respiratory Symptoms):

For a dog in the initial stage of CDV infection (upper respiratory symptoms only), antibiotics should be started to address or ward off any secondary bacterial infections, e.g., enrofloxacin (Baytril®) with clindamycin. The dog should be examined for infections and treated as needed, e.g., deworming, eye antibiotics, etc. A pure protein diet with probiotic addition(s) is recommended to foster healthy gut flora, e.g., chicken and yogurt. Treatment with NDV-induced serum from healthy donor dogs, or with two or more compositions that are not mixed and that each comprise serum from a healthy donor dog, should preferably commence concurrently.

Intermediate Stage (Early Neurological Symptoms):

For a dog displaying early neurological symptoms such as occasional seizures, an anti-seizure medication like phenobarbital should be administered, in addition to any antibiotics needed to address or ward off any secondary bacterial infections, e.g., enrofloxacin (Baytril®) with clindamycin. The dog should be examined and treated as needed, e.g., deworming, eye antibiotics, IV fluids for dehydration, etc. Steroids are preferably avoided for dogs showing early neurological symptoms. A pure protein diet with probiotic addition(s) is recommended to foster healthy gut flora, e.g., chicken and yogurt. For dogs hesitant to eat, dextrose by IV is suggested.

Begin treating with NDV-induced serum right away, as described below; keep the dog in as low-stress an environment as possible, preferably where it is able to walk around freely rather than being crated.

Advanced Stage (Late Neurological Symptoms):

In the advanced stage of CDV infection, symptoms arise from the viral infection as well as the dog's auto-immune response. For this reason, treatment of dogs showing late (i.e., severe) neurological symptoms preferably encompasses the treatment described above for the intermediate stage, and is augmented with steroid treatment (e.g., dexamethasone) to suppress the auto-immune response. This steroid treatment may go from 4-6 days depending on the animal's response. Such steroid treatment has the added benefit of ameliorating encephalitis pain and inflammation often seen in dogs with advanced stage CDV infection.

For advanced stage treatment, the first round of NDV-induced serum administration consists of two or more injections of donor dogs' NDV-induced serum, with each injection spaced eight hours apart. The donor dogs' NDV-induced serum should be kept separate and administered by intravenous (IV) injection one-at-a-time via IV port in the cephalic vein, i.e., first injection using NDV-induced serum from Dog A, second from Dog B, and so forth. For the second round of treatment, the time between injections should be 10 hours. Fluids should be administered by IV as needed to address dehydration.

After treatment (depending on the stage of CDV infection reached), the dogs should test negative for the virus after 5-6 weeks using widely available lab testing such as PCR.

Summary of Injection Schedule for Treating CDV Infection Using NDV-Induced Serum Treating Dogs with Only Upper Respiratory Symptoms (Initial Stage Distemper)

For dogs with only upper respiratory symptoms, the first round of treatment comprises injection of 4-6 mls or more preferably 5 mls of NDV-induced serum drawn from each donor dog, with the injections spaced 10 hours apart. Thus, 4-6 mls or more preferably 5 mls from Dog A followed 10 hours later with 4-6 mls or more preferably 5 mls from Dog B, and so on. The second round of treatment uses NDV-induced serum from the same donor dogs, but injections are spaced 12 hours apart.

Treating Dogs with Early Neurological Symptoms (Intermediate Stage Distemper)

For dogs exhibiting early neurological symptoms, follow the treatment outlined above for dogs that have only upper respiratory symptoms, but repeat the treatment at least approximately 24 hours later. If symptoms return or worsen, the treatment may be repeated again after at least approximately another 24 hours.

Treating Dogs with Late (i.e., Severe) Neurological Symptoms (Advanced Stage Distemper)

For dogs exhibiting late neurological symptoms, more aggressive treatment is recommended in the form of shortened intervals between NDV-induced serum administrations. In the first round of treatment, the time between injections should be shortened to 8 hours; in the second round, 10 hours.

EXAMPLES

Example 1

Thirteen dogs sharing the following characteristics were treated for CDV infection using NDV-induced serum as described here: diagnosis by lab testing such as PCR and observation of symptoms both, showed upper respiratory infection and neurological symptoms at the beginning of treatment, received vaccine within 6 weeks of becoming ill, but no earlier CDV vaccine. Following treatment for CDV infection showing neurological symptoms using NDV-induced serum as described here, eight of thirteen dogs survived—yielding a survival rate of 62%. Table 1 summarizes treatment outcomes for these dogs and the dogs in the other Examples below.

TABLE 1

Summary of treatment outcomes in 48 dogs described in Examples 1-7.

| Ex. # (Dog Grp #) | Diagnosis | | Symptoms of CDV infection | | Vaccine history | | Treatment outcome | | |
|---|---|---|---|---|---|---|---|---|---|
| | Lab test | Symptoms | Respiratory (early) | Neurological (intermed/ advance) | Vaccinated within 6 weeks of illness | No prior vaccine | Survived | Died w/ disease | Survival rate |
| 1 | x | x | x | x | x | | 8 | 5 | 62% |
| 2 | | x | | x | x | | 13 | 0 | 100% |
| 3 | x | x | | x | x | | 5 | 0 | 100% |
| 4 | | x | x | x | x | | 6 | 2 | 75% |
| 5 | | x | x | x | | x | 1 | 4 | 20% |
| 6 | x | x | | x | x | | 2 | 0 | 100% |
| 7 | x | x | x | x | | x | 2 | 0 | 100% |
| | | | | | | | 37 | 11 | 77% |

Example 2

Thirteen dogs sharing the following characteristics were treated for CDV infection using NDV-induced serum as described here: diagnosis by observation of symptoms, but not lab testing, showed neurological symptoms at the beginning of treatment, but not upper respiratory symptoms, received vaccine within 6 weeks of becoming ill, but no earlier CDV vaccine. Following treatment for CDV infection showing neurological symptoms using NDV-induced serum as described here, all thirteen dogs survived—yielding a survival rate of 100%. See Table 1 for treatment outcome summary.

Example 3

Five dogs sharing the following characteristics were treated for CDV infection using NDV-induced serum as described here: diagnosis by lab testing such as PCR and observation of symptoms both, showed neurological symptoms at the beginning of treatment, but not upper respiratory symptoms, received vaccine within 6 weeks of becoming ill, but no earlier CDV vaccine. Following treatment for CDV infection showing neurological symptoms using NDV-induced serum as described here, all five dogs survived—yielding a survival rate of 100%. See Table 1 for treatment outcome summary.

Example 4

Eight dogs sharing the following characteristics were treated for CDV infection using NDV-induced serum as described here: diagnosis by observation of symptoms, but not lab testing, showed neurological symptoms at the beginning of treatment as well as upper respiratory symptoms, received vaccine within 6 weeks of becoming ill, but no earlier CDV vaccine. Following treatment for CDV infection showing neurological symptoms using NDV-induced serum as described here, six of eight dogs survived—yielding a survival rate of 75%. See Table 1 for treatment outcome summary.

Example 5

Five dogs sharing the following characteristics were treated for CDV infection using NDV-induced serum as described here: diagnosis by observation of symptoms, but not lab testing, showed neurological symptoms at the beginning of treatment as well as upper respiratory symptoms, had not ever gotten any CDV vaccine prior to treatment. Following treatment for CDV infection showing neurological symptoms using NDV-induced serum as described here, one of five dogs survived—yielding a survival rate of 20%. See Table 1 for treatment outcome summary.

Example 6

Two dogs sharing the following characteristics were treated for CDV infection using NDV-induced serum as described here: diagnosis by observation of symptoms and lab testing such as PCR, showed neurological symptoms at the beginning of treatment but not upper respiratory symptoms, had gotten CDV vaccine within 6 weeks of becoming ill but not earlier. Following treatment for CDV infection showing neurological symptoms using NDV-induced serum as described here, both dogs survived—yielding a survival rate of 100% for Example 6. See Table 1 for treatment outcome summary.

Example 7

Two dogs sharing the following characteristics were treated for CDV infection using NDV-induced serum as described here: diagnosis by observation of symptoms, as well as lab testing such as PCR, showed neurological symptoms at the beginning of treatment as well as upper respiratory symptoms, and had never gotten any CDV vaccine prior to treatment. Following treatment for CDV infection showing neurological symptoms using NDV-induced serum as described here, both dogs survived. See Table 1 for treatment outcome summary.

Although the exact immunological mechanism remains unclear, administration of NDV-induced serum on a schedule, as disclosed here, bolsters the immune response of the sick dog. Until now, however, NDV-induced serum was thought not to be effective at treating dogs displaying late (i.e., severe) neurological symptoms of advanced stage distemper. Instead, skilled artisans would expect the only possible treatment to require a spinal tap. Further, a skilled artisan would have expected treatment following an NDV-induced serum protocol not to either save or effectively clear CDV from a dog exhibiting late neurological symptoms, as the inventor describes here.

CITATION LIST

Cited Patent Literature

U.S. Pat. No. 2,202,435 A
U.S. Pat. No. 3,285,817 A
U.S. Pat. No. 3,836,648 A
U.S. Pat. No. 4,992,272 A
U.S. Pat. No. 5,000,951 A
U.S. Pat. No. 5,807,840 A
U.S. Pat. No. 6,383,741 B2
U.S. Pat. No. 6,719,984 B1
U.S. Pat. No. 8,052,971 B2

Cited Non-Patent Literature

Bond E. Newcastle Disease Vaccine (NDV) treatment for canine distemper. 2010-01-15. Available at www.edbond.com/NDV_packet.pdf (last accessed 2018-07-25).

Bond E. Report on the Effectiveness of NDV Treatments. 2016-02-13. Available at http://www.kindheartsinaction.com/archives/1353 (last accessed 2018-07-25).

Bond E. Using the NDV Before Seizures. 2010-01-11. Available at www.kindheartsinaction.com/archives/313 (last accessed 2018-07-25).

Harkin K, Wilkerson M. Evaluation of the therapeutic efficacy and changes in cytokines in cerebrospinal fluid and plasma in dogs with canine distemper encephalitis treated with intrathecal live Newcastle Disease Virus vaccine [Research Proposal]. 2014. Available at www.maddiesfund.org (last accessed 2018-07-25).

Sears A. NDV-induced Serum. 2011. Available at www.kindheartsinaction.com/archives/82 (last accessed 2018-07-25).

Vahlenkamp T. Canine Distemper and Other Canine Viral Infections, in Textbook of Veterinary Internal Medicine. 2016. Pages 1006-9.

The invention claimed is:

1. A method of treating a mammal exhibiting seizures caused by an advanced stage canine distemper virus (CDV) infection, comprising:
   administering compositions from each of two or more separate donor mammals intravenously to the mammal exhibiting seizures caused by the advanced stage CDV infection,
   the compositions being administered separately and not mixed prior to administration,
   each composition comprising serum collected from a member of the same species previously injected with Newcastle Disease Vaccine (NDV),
   wherein treating the mammal exhibiting seizures caused by the advanced stage CDV infection with the compositions results in the mammal surviving and testing negative for CDV infection.

2. The method of claim 1 wherein the mammal is a canid, a mustelid, a procyonid, or a felid that is larger than a domestic cat.

3. The method of claim 2, wherein the mammal is a domestic dog, wolf, coyote, fox, jackal, dingo, weasel, badger, otter, mink, marten, polecat, wolverine, raccoon, coati, olingo, olinguito, ringtail, cacomistle, kinkajou, bobcat, wildcat, ocelot, lynx, cheetah, serval, leopard, snow leopard, cougar, puma, tiger, or lion.

4. The method of claim 1, wherein each composition is administered by intravenous (IV) injection via an IV port in the cephalic vein.

5. The method of claim 1, wherein the mammal is further treated with a steroid treatment.

6. The method of claim 1, further comprising:
   injecting the mammal with the compositions in at least two rounds of treatment, wherein:
   administering a first round of treatment comprising injecting the mammal with the compositions from each of the two or more separate donor mammals, the compositions being administered about eight hours apart; and
   administering a second round of treatment comprising injecting the mammal with the compositions from each of the two or more separate donor mammals, the compositions being administered about ten hours apart.

7. The method of claim 1, wherein the each of two or more separate donor mammals are injected with NDV eleven hours before the compositions are collected.

8. A method of treating a dog exhibiting seizures caused by an advanced stage canine distemper virus (CDV) infection, comprising:
   separately administering compositions from each of two or more separate donor dogs intravenously to the dog exhibiting seizures caused by the advanced stage CDV infection,
   the compositions being administered separately and not mixed prior to administration,
   wherein the donor dogs previously have been injected with Newcastle Disease Vaccine (NDV).

9. The method of claim 8, wherein the administering step is carried out without the use of any spinal tap procedure.

10. The method of claim 9, wherein each donor dog is 10-48 months old, of mixed breed, weighing 40-120 pounds, and without mange, mites, arthritis, or any autoimmune disorders.

11. The method of claim 10, wherein each donor dog is selected from a black labrador mix and border collie mix.

12. The method of claim 11, wherein each donor dog has been free of at least one of immune suppressants, corticosteroids, or antihistamines for at least 14 days before NDV injection.

13. The method of claim 8, wherein each composition is administered by intravenous (IV) injection via an IV port in the cephalic vein.

14. The method of claim 8, wherein the dog is further treated with a steroid treatment.

15. The method of claim 8, further comprising:
   injecting the dog with the compositions in at least two rounds of treatment, wherein:
   administering a first round of treatment comprising injecting the dog with the compositions from each of the two or more separate donor dogs, the compositions being administered about eight hours apart; and
   administering a second round of treatment comprising injecting the dog with the compositions from each of the two or more separate donor dogs, the compositions being administered about ten hours apart.

16. The method of claim 8, wherein the each of two or more separate donor dogs are injected with NDV eleven hours before the compositions are collected.

17. An article of manufacture for treating a mammal exhibiting seizures caused by an advanced stage canine distemper virus (CDV) infection, intravenously, comprising:
   compositions from each of two or more separate donor mammals, the compositions being administered separately and not mixed prior to intravenous administration to the mammal exhibiting seizures caused by an advanced stage canine distemper virus (CDV) infection, and each donor mammal being a member of the same species previously earlier injected with Newcastle Disease Vaccine (NDV).

18. The article of manufacture of claim 17, wherein the mammal is a domestic dog, wolf, coyote, fox, jackal, dingo, weasel, badger, otter, mink, marten, polecat, wolverine, raccoon, coati, olingo, olinguito, ringtail, cacomistle, kinkajou, bobcat, wildcat, ocelot, lynx, cheetah, serval, leopard, snow leopard, cougar, puma, tiger, or lion.

19. The article of manufacture of claim 17, wherein each donor mammal is 10-48 months old, of mixed breed, weighing 40-120 pounds, without mange, mites, arthritis, or any autoimmune disorders.

20. The article of manufacture of claim 19, wherein each donor mammal is selected from a black labrador mix and border collie mix.

21. The article of manufacture of claim 19, wherein each donor mammal has been free of at least one of immune suppressants, corticosteroids, or antihistamines for at least 14 days before NDV injection.

22. A method for treating a dog with Canine Distemper Virus (CDV), the method comprising:

determining that the dog has a CDV infection;

determining that the dog is in an advanced stage of the CDV infection based on the dog having at least one seizure;

obtaining a first serum by:

injecting a first donor dog with Newcastle Disease Vaccine (NDV);

drawing a first blood sample from the first donor dog 10 to 12 hours after injecting the first donor dog with NDV;

centrifuging the first blood sample; and extracting the first serum from the centrifuged first blood sample;

obtaining a second serum by:

injecting a second donor dog with NDV;

drawing a second blood sample from the second donor dog 10 to 12 hours after injecting the second donor dog with NDV;

centrifuging the second blood sample; and extracting the second serum from the centrifuged second blood sample;

administering a first treatment round to the dog by:

injecting the first serum intravenously;

waiting approximately 8 hours; and injecting the second serum; and administering a second treatment round to the dog by:

injecting the first serum intravenously;

waiting approximately 10 hours; and injecting the second serum.

* * * * *